United States Patent [19]
Nalbantoglu et al.

[11] Patent Number: 5,894,078
[45] Date of Patent: Apr. 13, 1999

[54] TRANSGENIC MOUSE EXPRESSING C-100 APP

[75] Inventors: Josephine Nalbantoglu, Mount Royal; Jean-Pierre Julien, Montreal; Matthew Shapiro, Outremont, all of Canada

[73] Assignee: Advanced Bioconcept, Inc., Montreal, Canada

[21] Appl. No.: 08/607,124

[22] Filed: Feb. 26, 1996

[51] Int. Cl.⁶ .............................. C12N 5/00; C12N 15/00
[52] U.S. Cl. ..................... 800/2; 800/DIG. 1; 424/9.2; 435/320.1
[58] Field of Search .................. 800/2, DIG. 1; 435/320.1, 172.3; 424/9.1

[56] References Cited

U.S. PATENT DOCUMENTS 5,612,486  3/1997  McConlogue et al. .

FOREIGN PATENT DOCUMENTS

WO 93/14200  7/1993  WIPO .
WO 94/12627  6/1994  WIPO .

OTHER PUBLICATIONS

Eddleston and Mucke, Neuroscience 54:15–36, 1993.
Frederickson, Neurobiology of Aging 13:239–253, 1992.
Fukuchi et al., Annals New York Academy of Sciences, pp. 217–223.
Gordon et al., Proc. Natl. Acad. Sci. USA 77:7380, 1980.
Higgins et al., Ann. Neurol. 35:598–607, 1994.
Higgins et al., Proc. Natl. Acad. Sci. USA 92:4402–4406, 1995.
Jucker et al., Science 255:1443–1445, 1992.
Julien et al., Mol. Brain Res. 1:243–250, 1986.
Kammesheidt et al., Proc. Nalt. Acad. Sci. USA 89:10857–10861, 1992.
Kang, et al., Nature 325:733–736, 1987.
Kawabata et al., Nature 354:476–478, 1991.
Kawabata et al., Nature 356:23, 1992.
LaFerla et al., Nature Genetics 9:21–30, 1995.
Lamb et al., Nature Genetics 5:22–30, 1993.
Lamb, Nature Genetics 9:4–6, 1995.
Lannfelt et al., Behavioural Brain Research 57:207–213, 1993.
Levy–Lahad et al., Science 269:973–977, 1995.
Marx, Science 253:266–267, 1991.
Meaney, Science 239:766–768, 1988.
Moran et al., Proc. Natl. Acad. Sci. USA 92:5341–5345, 1995.
Mrak et al., Human Pathology 26:816–823, 1995.
Pearson and Choi, Proc. Natl. Acad. Sci. USA 90:10578–10582, 1993.
Quan et al., Nature 352:239–241, 1991.
Rogaev et al., Nature 376:775–778, 1995.
Sandhu et al., J. Biol. Chem. 2666:21331–21334, 1991.
Sherrington et al., Nature 375:754–760, 1995.
Tanzi, The New England Journal of Medicine 332:1512–1513, 1995.
Wirak et al., Science 255:1445, 1992.
Wirak et al., Science 253:323–325, 1991.
Yamaguchi et al., NeuroReport 2:781–784, 1991.
Aguzzi et al., Brain Pathology 4:3–20, 1994.
Duff, Journal of the Florida Medical Association 91:625–8, 1994.
Duff and Hardy, Nature 373:476–7, 1995.
Erikson, Scientific American 265:34, 1991.
Price and Sisodia, Annual Review of Medicine 45:435–46, 1994.
Price et al., Progress in Clinical & Biological Research 379:271–87, 1992.
Rennie, Scientific American 266:20–6, 1992.
Robertson, Nature 356:103, 1992.
Selkoe, Nature 354:432–3, 1991.
Sisodia et al., Neuroimaging Clinics of North America 5:59–68, 1995.
Sofroniew and Staley, Trends in Neurosciences 14:513–4, 1991.
Felsenstein et al (1995) Alz. Parkinson's Diseases, I. Hanin, ed. Plenum Press, NY, 401–409.
Podlisny et al (1992) Neurobio. Aug. 13, 561–567.
Games et al (1992) Neurobio. Aug. 13, 569–576.
Jänne et al (1992) Annals of Med. 24, 273–280.
Julien et al (1987) Genes & Devel. 1, 1085–1095.

*Primary Examiner*—Deborah Crouch
*Attorney, Agent, or Firm*—Clark & Elbing LLP

[57] ABSTRACT

A transgenic mouse whose genome comprises a DNA sequence encoding the carboxy-terminal 100 amino acids of the human β-amyloid precursor protein C-100 APP) inserted into exon I of the neurofilament gene such that all or part of exon I has been deleted is disclosed. Expression of the nucleic acid sequence is under the control of neurofilament L-gene regulatory region. The mouse as a result of the expression exhibits a brain morphology of an increased amyloid accumulation, and increase in reactive astrocytes, an increased microglial activation and a decreased number of neurons, and also exhibits spatial memory impairment.

16 Claims, 11 Drawing Sheets

| Factors | All measures | Latency | Total distance | Distance to The platform | Correct trials |
|---|---|---|---|---|---|
| | df | F | F | F | F |
| Age | 1,38 | 6.62* | 4.39* | 7.98** | 8.92***# |
| Group | 1,38 | 10.79*** | 8.27** | 7.64** | 12.12****# |
| Age*Group | 1,38 | 2.91 | 0.21 | 0.08 | 4.2* |
| task | 3,36 | 28.45**** | 34.23**** | 14.1**** | 12.01**** |
| task*age | 3,36 | 2.89* | 2.23 | 2.88*# | 3.33* |
| task*group | 3,36 | 2.39 | 1.06 | 4.35**# | 2.22 |
| task*age*group | 3,36 | 0.81 | 2.96* | 0.87 | 0.31 |
| day | 6,33 | 13.08**** | 35.94**** | 11.19**** | 4.47*** |
| day*age | 6,33 | 1.17 | 0.56 | 0.74 | 0.80 |
| day*group | 6,33 | 3.09* | 3.67** | 2.59* | 0.73 |
| day*age*group | 6,33 | 1.42 | 1.42 | 0.90 | 0.81 |
| task*day | 18,21 | 1.14 | 2.65* | 2.44* | 2.16 |
| task*day*age | 18,21 | 2.16* | 2.44* | 0.79 | 1.90 |
| task*day*group | 18,21 | 2.46* | 3.97*** | 2.91**# | 1.79 |
| task*day*age*group | 18,21 | 1.61 | 2.32* | 1.92 | 1.81 |

*p<.05
**p<.01
***p<.005
****p<.001
-equal instead of less

Fig. 6

TRANSGENIC MOUSE EXPRESSING C-100 APP

BACKGROUND OF THE INVENTION

This invention relates to transgenic animal models of Alzheimer's disease.

Transgenic animal models have recently become valued tools in the elucidation of human disease processes as well as in the characterization of therapeutic drugs for disease treatment. In the case of Alzheimer's disease, a disease which currently affects 3 million persons and which is predicted to increase 50% by the year 2000, a particular need for accurate animal models exists, as highlighted by several factors. First, little is known about the etiology of the disease. Although specific proteins (including the beta-amyloid precursor protein of chromosome 21, the apolipoprotein E ε4 isoform of chromosome 19, and related unknown proteins recently cloned from chromosomes 1 and 14), as well as specific gene mutations (for example, specific mutations of the beta-amyloid precursor protein) have been found to be associated with certain forms of Alzheimer's disease, their roles in disease pathology are not well understood. In addition, due to the existence of disease subgroups and the disease's debilitating nature, Alzheimer's patients are difficult to diagnose or to differentiate from patients exhibiting other forms of dementia. Finally, in terms of morphological changes, beta-amyloid accumulation within the brain is generally associated with Alzheimer's disease, but the degree of beta-amyloid variation both within a patient population and as compared to age-matched control subjects is significant. Moreover, it remains controversial whether beta-amyloid accumulation is actually causal to neuronal cell loss or to the cognitive deficits characteristic of Alzheimer's disease.

The pain of Alzheimer's disease results directly from the memory loss and cognitive deficits suffered by the patient. These eventually result in the patient's loss of identity, autonomy, and freedom. As a step toward curing this disease, alleviating its symptoms, or retarding its progression, it would be desirable to develop a transgenic animal model exhibiting the main debilitating phenotype of Alzheimer's disease, that is, memory loss, expressed concomitantly with the neuropathological correlates of Alzheimer's disease, for example, beta-amyloid accumulation, increased glial reactivity, and hippocampal cell loss.

SUMMARY OF THE INVENTION

In general, the invention features a transgenic, non-human mammal that includes an Alzheimer's-associated nucleic acid sequence operably linked to a neurofilament L gene that substantially lacks exon 1, the Alzheimer's-associated nucleic acid sequence (a) being positioned in a region that, in the naturally-occurring neurofilament L gene, includes all or a part of exon 1 and (b) being expressed under the control of the neurofilament L regulatory region.

In preferred embodiments, the expression of the Alzheimer's-associated nucleic acid is limited to all or a part of the mammal's nervous system; the Alzheimer's-associated nucleic acid expresses an amyloid protein (for example, a human amyloid protein such as the C-terminal 100 amino acids of the human beta-amyloid protein); the mammal exhibits an increase in amyloid accumulation in the central nervous system (for example, in the brain); the mammal exhibits spatial memory impairment; the mammal exhibits no substantial motor defects; and the mammal is a rodent (for example, a mouse).

In a second aspect, the invention features a transgenic non-human mammal, the mammal exhibiting a spatial memory impairment.

In preferred embodiments of this second aspect, the mammal exhibits no substantial motor defects; the spatial memory impairment progressively worsens with the age of the mammal; the mammal exhibits no substantial anxiety; the mammal exhibits an increase in amyloid accumulation in the central nervous system (for example, in the brain); the mammal exhibits an increase in reactive astrocytes in the brain; the mammal exhibits an increase in microglial activation; the mammal exhibits a decreased number of neurons (preferably, at least a 15% decrease in neurons in the hippocampus); the mammal is capable of transferring the spatial memory impairment trait to its offspring in a Mendelian fashion; the mammal expresses an Alzheimer's-associated protein (for example, an amyloid protein, and preferably a human amyloid protein, such as the C-terminal 100 amino acids of the human beta-amyloid protein); the expression of the Alzheimer's-associated protein is limited to all or a part of the mammal's nervous system; the Alzheimer's-associated protein is expressed under the control of a neurofilament L regulatory region and preferably is an amyloid protein (for example, the C-terminal 100 amino acids of the human beta-amyloid protein); and the mammal is a rodent (for example, a mouse).

In a third aspect, the invention features a method of producing a transgenic non-human mammal that exhibits a spatial memory impairment, involving (a) introducing into a fertilized oocyte of the mammal a nucleic acid that includes an Alzheimer's-associated nucleic acid under the control of a nervous system-specific regulatory region;

(b) transplanting the fertilized oocyte into a pseudopregnant mammal;

(c) allowing the fertilized oocyte to develop to term; and (d) identifying at least one offspring containing the nucleic acid that includes the Alzheimer's-associated nucleic acid under the control of the nervous system-specific regulatory region.

In preferred embodiments, the Alzheimer's-associated nucleic acid expresses an amyloid protein (for example, the C-terminal 100 amino acids of the human beta-amyloid protein); the nervous system-specific regulatory region is a neurofilament L regulatory region; and the mammal is a rodent (for example, a mouse).

In a fourth aspect, the invention features a method for expressing a nucleic acid sequence of interest in a nervous system-specific manner, involving operably linking the nucleic acid sequence of interest to a neurofilament L gene that substantially lacks exon 1, the nucleic acid sequence of interest being positioned in a region that, in the naturally-occurring neurofilament L gene, includes all or a part of exon 1 and the nucleic acid sequence of interest being expressed under the control of the neurofilament L regulatory region.

In preferred embodiments, the expression occurs in a transgenic, non-human mammal (for example, a rodent such as a mouse); the nucleic acid sequence of interest is an Alzheimer's-associated nucleic acid (for example, an amyloid protein, for example, the C-terminal 100 amino acids of human beta-amyloid protein); and the expression occurs in the brain and spinal cord.

In a fifth aspect, the invention features a transgene including (a) a nucleic acid sequence of interest linked to (b) a neurofilament L gene that substantially lacks exon 1, the nucleic acid sequence of interest being positioned in a region that, in the naturally-occurring neurofilament L gene, includes all or a part of exon 1 and the nucleic acid sequence of interest being expressed under the control of the neurofilament L regulatory region.

In preferred embodiments, the nucleic acid sequence of interest is an Alzheimer's-associated nucleic acid (for example, an amyloid protein, for example, the C-terminal 100 amino acids of human beta-amyloid protein); and expression occurs in the brain and spinal cord.

In a sixth aspect, the invention features a method of testing a substance for efficacy in the treatment of Alzheimer's disease, involving exposing a transgenic non-human mammal of the invention to the substance and determining the extent of spatial memory impairment exhibited by the mammal following substance exposure, a decrease in the spatial memory impairment indicating a substance useful for the treatment of Alzheimer's disease. Also included in the invention are substances identified by this method.

In preferred embodiments, the mammal expresses an amyloid protein (for example, a human amyloid protein, for example, the C-terminal 100 amino acids of the human beta-amyloid protein); and the mammal is a rodent (for example, a mouse).

As used herein, by "transgenic" is meant any mammal which includes a nucleic acid sequence which is inserted by artifice into a cell and becomes a part of the genome of the animal that develops from that cell. Such a transgene may be partly or entirely heterologous to the transgenic animal. Although transgenic mice represent a preferred embodiment of the invention, other transgenic mammals including, without limitation, transgenic rodents (for example, hamsters, guinea pigs, rabbits, and rats), and transgenic pigs, cattle, sheep, and goats may be constructed by standard techniques and are included in the invention.

By "spatial memory impairment" is meant a statistically significant reduction in the performance of adult animals (for example, mice of approximately 8 months of age or older) on spatial memory tests, for example, the tests described herein or standard autoshaping, two-object discrimination, radial arm maze, or forced alteration T-maze tests. Statistical significance is preferably measured by the technique of analysis of variance followed by post-hoc tests such as Dunnet's or Student's T-tests, but may be measured by any other standard statistical equation.

By "no substantial motor defects" is meant that there is no statistically significant difference (as measured above) between groups of adult transgenic animals and equivalent groups of wild-type control animals in motor performance tests; such tests include those described herein or those in which measurements are carried out in locomoter activity boxes.

By "no substantial anxiety" is meant that there is no statistically significant difference (as measured above) between groups of adult transgenic animals and equivalent groups of wild-type control animals in anxiety tests; such tests include those described herein or the Thatcher-Britton novelty conflict test.

By "amyloid accumulation" is meant any significant increase in the presence of amyloid (for example, human beta-amyloid) in the nervous system of the transgenic animal. By a significant increase is meant the detection of more than 4 accumulations (and, preferably, at least 5 accumulations) of extracellular amyloid material per coronal section of brain examined at the level of the hippocampal formation. Amyloid accumulations are generally present as diffuse or dense plaques, but may also be present as fibrils.

By "reactive astrocyte" is meant an increase in the size of a cell expressing glial fibrillary acidic protein.

By "microglial activation" is meant a stereotypic pattern of cellular responses including, but not limited to, microglial proliferation, increased or de novo expression of immunomolecules, recruitment to sites of injury, and release of inflammatory mediators.

By "Alzheimer's-associated protein" is meant any polypeptide product, regardless of length or post-translational modification, that has been, or will be, found to be associated with Alzheimer's disease or its symptoms. Such proteins include, without limitation, any amyloid protein or Alzheimer's-associated amyloid fragment or precursor (for example, the human beta-amyloid protein and the human C-100 APP fragment), the apolipoprotein E $\epsilon$4 protein, and the proteins of presenilin 1 (S182) (Sherrington et al., Nature 375:754–760, 1995) and presenilin 2 (STM2) (Levy-Lahad et al., Science 269:973–977, 1995; Rogaev et al., Nature 376:775–778, 1995). The nucleic acid sequence encoding an Alzheimer's-associated protein is termed an "Alzheimer's-associated gene."

By "nervous system-specific" is meant that expression of a nucleic acid sequence occurs substantially in a nervous system tissue (for example, the brain or spinal cord), and does not substantially occur in other tissues of the animal. Preferably, the expression of the nucleic acid sequence in the nervous system tissue represents at least a 5-fold, more preferably, a 10-fold, and, most preferably, a 100-fold increase over expression in non-nervous system tissue.

By "regulatory region" is meant a sequence which is minimally necessary for directing transcription and, if appropriate, translation of an associated nucleic acid coding sequence. The term may also include auxiliary sequences that mediate gene expression in response to an external or internal stimulus, for example, expression that is inducible (for example, by temperature or a chemical stimulus) or expression that is tissue-specific (for example, nervous system-specific) or developmental stage-specific. "Regulatory region" sequences are generally located 5' (or "upstream") of the nucleic acid coding sequence, but may be located within or 3' (or "downstream") of the coding sequence.

By "introducing into a fertilized oocyte" is meant to encompass any method by which a transgene may be introduced into a mammalian oocyte including, without limitation, microinjection and retroviral infection.

By "substantially lacking exon 1" is meant that the neurofilament gene does not contain more than 60 nucleotides, and preferably does not contain more than 30 nucleotides, of exon 1.

By "treatment of Alzheimer's disease" is meant the ability to reduce, prevent, or retard the onset of any symptom associated with Alzheimer's disease, particularly those resulting in spatial memory impairment, increased amyloid accumulation (for example, in the brain), increased reactive astrocytes (for example, in the brain), increased microglial activation, or decreased neuron number (for example, in the hippocampus).

By "operably linked" is meant that a nucleic acid sequence and a regulatory sequence(s) are connected in such a way as to permit expression of that nucleic acid sequence.

As described herein, the current invention provides a number of advantages. First, because transgenic animals are generally useful for the investigation of specific biological processes and for reproducing particular aspects of human disease, the transgenic animals of the invention provide an important and accurate means for screening drugs to isolate therapeutic agents. In particular, the spatially-impaired transgenic animals that are described for the first time herein have the advantage of mimicking the memory loss and cognitive defects observed in patients with Alzheimer's disease. In addition, the progress of this critical symptom, i.e., the presence of specific spatial memory impairments, is easily observable in the same animal over time, since its examination does not require animal sacrifice. Accordingly, the efficacy of a particular therapy may be examined in the same animal at different disease stages. In addition, as these spatial memory impairments are observable in the mice of the invention as early as 8 months of age and are progressive with time, this animal model is also useful for the testing of palliative therapies which delay the appearance of further cognitive deficits. Importantly, because this invention provides a transgenic animal model of Alzheimer's disease with measurable spatial memory loss, compounds may be screened to identify those which alleviate this symptom, even absent knowledge of the symptom's underlying biological cause.

In addition, although not strictly required for drug screening, the associated neuropathological symptoms exhibited by the transgenic animal models described herein provide the unique advantage of allowing the investigation of the etiology of Alzheimer's disease. For example, the appearance of beta-amyloid accumulations, glial hyperactivity, and/or hippocampal cell loss may be correlated with the appearance of specific behavioral impairments within individuals or groups of animals. In addition, treatments which are shown to improve memory function may be tested for their ability to selectively improve certain pathological symptoms.

Another advantage of this invention is the ease with which these transgenic animals are bred to produce identical transgenic offspring. Unlike some transgenic animal models, the above described animals transmit the beta-amyloid transgene to 100% of their offspring, making this a highly reproducible model system. Also, because these transgenic animals may be bred as readily as control animals and because they produce similar size litters, the animals of the invention may be generated in sufficient quantity to make them widely and rapidly available to researchers in this field.

With respect to the production of the present transgenic mice, further advantages are provided by the use of the C3B6 F1 strain described herein because control mice of this strain learn new tasks quickly and thus serve as good comparison strains for spatially impaired transgenic animals. In addition, use of F1 hybrids (rather than inbred mice) increases the vigor of the eggs collected for DNA injection and therefore increases survival rates following injection.

With respect to the construct used to generate the transgenic animals, the use of the neurofilament L promoter and gene also provides additional advantages. First, this construct is active only in central nervous system tissue. In addition, the neurofilament gene has the advantage of being expressed mainly in neurons of the central nervous system and not in glial cells. Furthermore, the use of all but a portion of exon 1 of the neurofilament gene has the advantage of including most of the upstream and downstream regulatory sequences responsible for controlling the level of inserted transgene expression. The deletion of a portion of exon 1 also has the advantage of providing an ideal site for transgene insertion, for example, for the insertion of the C-100 fragment of the human beta-amyloid gene.

As described herein, preferred transgenic animals according to the invention include the C-100 APP fragment of the human beta-amyloid gene. This fragment has the advantage of possessing its own termination codon at position 696 and therefore directing transgene expression only (i.e., in the absence of the remaining exons of the construct derived from the neurofilament gene). In addition, this gene is known to produce only the C-terminal amino acids of the human beta-amyloid precursor protein (C-100 APP), a fragment which has been shown to aggregate and form insoluble fibrils in vitro. By this approach, the transgenic animal receives the potentially damaging cleavage product of APP, while eliminating the need for proper processing by proteases or other enzymes specific for cleaving the precursor to its amyloidogenic fragment. Moreover, the addition of a polyadenylation site (for example, an SV40 polya site) to the C-100 APP gene at position 696 (as described herein) has the advantage of stabilizing the transcribed MRNA. This polyadenylation sequence also facilitates the carrying out of Northern blots (i.e., assays used to detect RNA within transgenic animal tissue) using only polya-extended RNA, and thereby restricting the analysis to messenger RNA. The addition of the polyadenylation site further differentiates the endogenous rat beta-amyloid MRNA from the human transgene MRNA by increasing the molecular size difference between the two on Northern blots.

Other features and advantages of the invention will be apparent from the following detailed description and from the claims.

DETAILED DESCRIPTION

The drawings will first be described.

DESCRIPTION OF THE DRAWING

FIG. 6 is a table summarizing behavioral data for control and transgenic animals.

Figure 1:
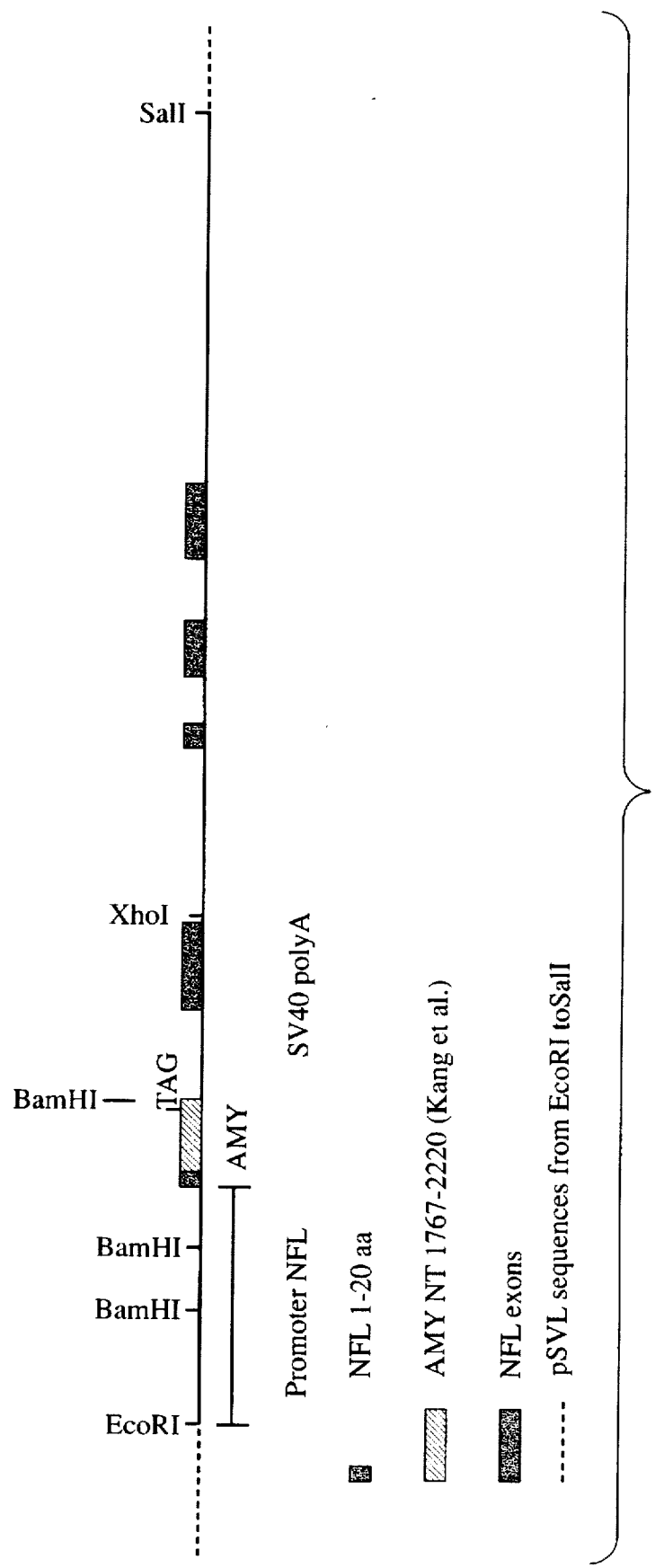
FIG. 1 is a schematic drawing showing the construction of the neurofilament promoter/C-100 amyloid precursor protein DNA fragment derived from PNFL (neurofilament L; NFL) and pC-100 APP (amyloid precursor protein; AMY). This construct was microinjected into mouse fertilized oocyte pronuclei as described herein.

The transgenic animals of the invention are described in detail below. In general, these animals are produced by first creating a construct that includes a promoter that directs nervous system-specific expression linked to a gene associated with Alzheimer's disease progression. This construct is amplified in bacterial cells, purified, and injected into isolated mouse oocytes, which are then implanted into pseudopregnant females. Resulting offspring that have incorporated the foreign gene into their genomes are identified. From these founder mice, several distinct animal lines are produced by breeding with wild-type animals. The heterozygotes produced are then bred together to obtain homozygotes expressing the transgene on both chromosomes. These homozygotes may be bred indefinitely and are used in a series of test to characterize the transgenic mouse phenotype.

The transgenic animals described herein exhibit impairments in spatial memory in the absence of changes in motor and other behavioral parameters, after having been genetically modified with a gene known to be associated with Alzheimer's disease, such as beta-amyloid. The use of the C-100 APP gene is preferred.

Construction of the Neurofilament Promoter/C-100 Amyloid Precursor Protein (NFL/C-100 APP) Plasmid The neurofilament promoter/C-100 APP construct used to generate animals according to the invention was produced as follows. The human beta-amyloid CDNA of Kang et al. (Nature 325:733–736, 1987) was treated with BglII and BamHI, and a fragment encoding amino acids 591 to 695 (numbered according to APP695; Kang et al., supra) was first inserted into the BamHI site of the vector PSVL (Pharmacia, Upsala, Sweden), and then excised with SmaI and SalI. This fragment was then inserted into a second plasmid containing the NFL gene (described by Julien et al., Mol. Brain Res. 1:243–250, 1986), which had been digested with SmaI and XhoI. In so doing, the CDNA fragment encoding human beta-amyloid amino acids 591 to 695 was placed under the transcriptional control of the human neurofilament (NFL) promoter, replacing NFL nucleotides 2493 to 3508, and leaving the remainder of the NFL gene (i.e., from the first intron to the 3' noncoding sequence) intact.

Following its construction, the NFL/C-100 APP transgene construct was amplified by transforming bacterial cells using standard techniques. Plasmid DNA was then purified and treated with EcoRI and SalI to remove the endogenous bacterial sequences. A 10 kb EcoRI/SalI fragment was purified by agarose gel electrophoresis in preparation for microinjection.

Microinjection of NFL/C-100 APP into Mouse Zygotes and Analysis of Founder Mice

A 10 kb EcoRI/SalI fragment of the NFL/C-100 APP DNA isolated above was microinjected into the male pronuclei of fertilized mouse eggs derived from the C3B6 F1 strain, using the techniques described in Gordon et al. (Proc. Natl. Acad. Sci. USA 77:7380, 1980). The eggs were transplanted into pseudopregnant female mice for full-term gestation, and the resultant litters consisted of a total of 21 mice.

At 3 to 4 weeks of age, a small piece of tail tissue was cut from each of these mice, and chromosomal DNA was extracted. The DNA was then analyzed for the presence of integrated human APP sequences using Southern blotting and a radioactive human amyloid probe that consisted of a BglII/PvuII fragment of the human CDNA of Kang et al. (supra). Southern hybridization was performed according to standard techniques (Molecular Cloning: A Laboratory Manual, Maniatis et al., Cold Spring Harbor Press, Cold Spring Harbor, N.Y., 1982), using chromosomal DNA digested with BamHI, an enzyme that was predicted to cut the transgene into a 900 base pair fragment (see FIG. 1).

Figure 2:
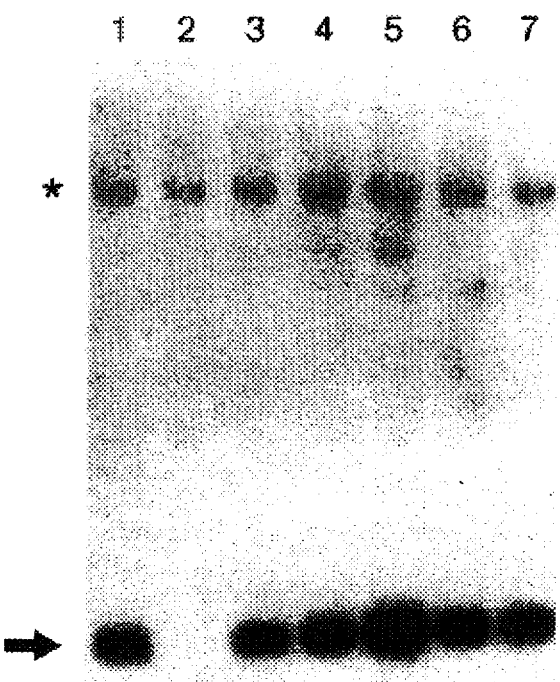
FIG. 2 is a representative Southern blot of DNA isolated from the tails of transgenic mice of the invention. The DNA was digested with BamH1, and the restriction fragments hybridized with a human beta-amyloid DNA probe. The band indicated by the arrow represents the 900 base-pair fragment of human beta-amyloid that is absent from control mice. The star indicates the large mouse beta-amyloid precursor gene fragment which reacts weakly with the human probe.

FIG. 2 shows the results of such an analysis. The arrow shows the 900 base pair fragment detected in the transgenic animals corresponding to the NFL/C-100 APP fragment (lanes 1 and 3–7). Also, as shown, this fragment was absent from the normal mouse chromosome (lane 2). The star indicates a large mouse gene fragment which reacted only weakly with the human probe (all lanes). Accordingly, a fragment of DNA of the same size and containing APP sequences does not exist in the mouse genetic material, demonstrating the authenticity of the integrated transgene. Of the 21 animals produced, 7 were transgenic mice that transferred the integrated gene in a Mendelian fashion to their offspring. One mosaic animal was identified which did not transfer the transgene. The copy number of the transgene varied between 5 and 20 integrated copies per animal.

Figure 3:
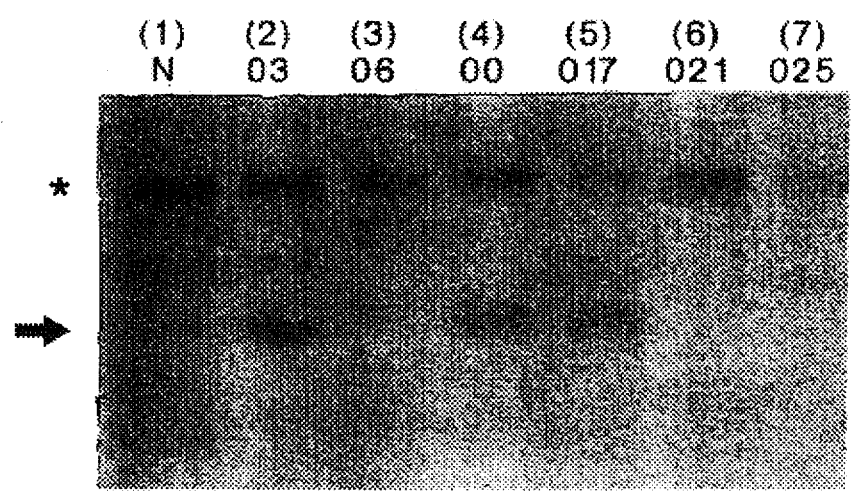
FIG. 3 is a Northern blot of total MRNA from the brains of six transgenic mice of the invention probed with the human beta-amyloid gene (lanes 2–7). Of these transgenic lines, only three expressed human beta-amyloid messenger RNA at levels equivalent to that of mouse beta-amyloid MRNA. P-amyloid-derived transcripts are indicated by the arrow. "N" represents a non-transgenic animal.

Expression of the C-100 APP Messenger RNA in Transgenic Mice Containing the Integrated NFL/C-100 APP Construct To demonstrate the capability of the NFL/C-100 APP construct to produce messenger RNA in transgenic animals, the mice described above were sacrificed by carbon dioxide inhalation and dissected to remove different tissues. Total RNA was then prepared from the tissues, and the RNA electrophoresed on a 1.2% agarose gel according to standard protocols (*Molecular Cloning: A Laboratory Manual*, Maniatis et al., Cold Spring Harbor Press, Cold Spring Harbor, N.Y., 1982). The RNA was then analyzed for the presence of amyloid message by hybridization with the radioactively labeled human amyloid probe described above. Due to the high similarity between the human and mouse amyloid sequences, the human probe readily detected the mouse full-length messenger RNA. However, since the C-100 APP transgene contained only a portion of the total APP gene, the messenger RNA produced from the transgene was easily separated and distinguished from the mouse endogenous sequence (see FIG. 3). Of seven different transgenic lines, only three expressed messenger RNA at levels sufficient to be detected by Northern analysis using total brain tissue RNA (lanes 2, 4, and 5, FIG. 3). PCR, which is considerably more sensitive than classical Northern blotting, was not utilized in these experiments because preferred transgenic animals were those which expressed the amyloid fragment at a high enough level to be detectable by Northern blotting.

Figure 4:
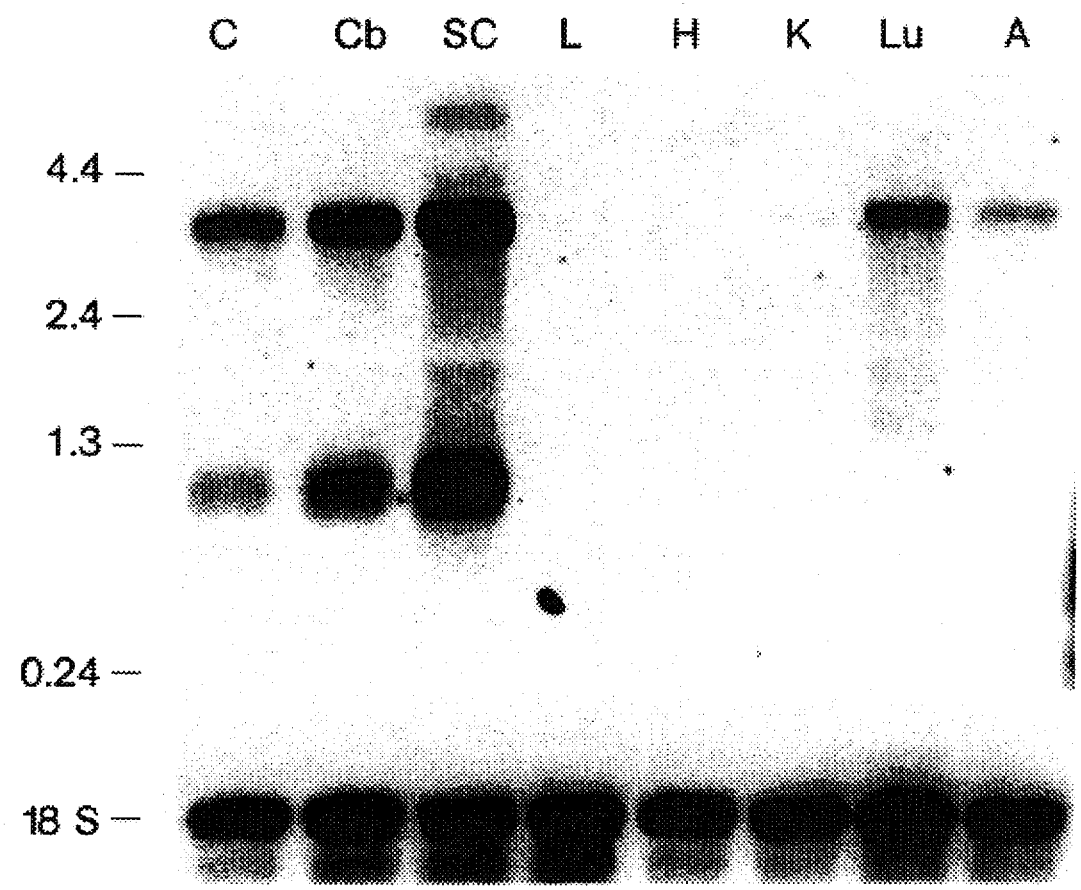
FIG. 4 is a Northern blot analysis of total RNA isolated from various transgenic mouse tissues. As shown, tissue-specific expression of the human beta-amyloid construct was observed only in central nervous system tissues.
Figure 5:
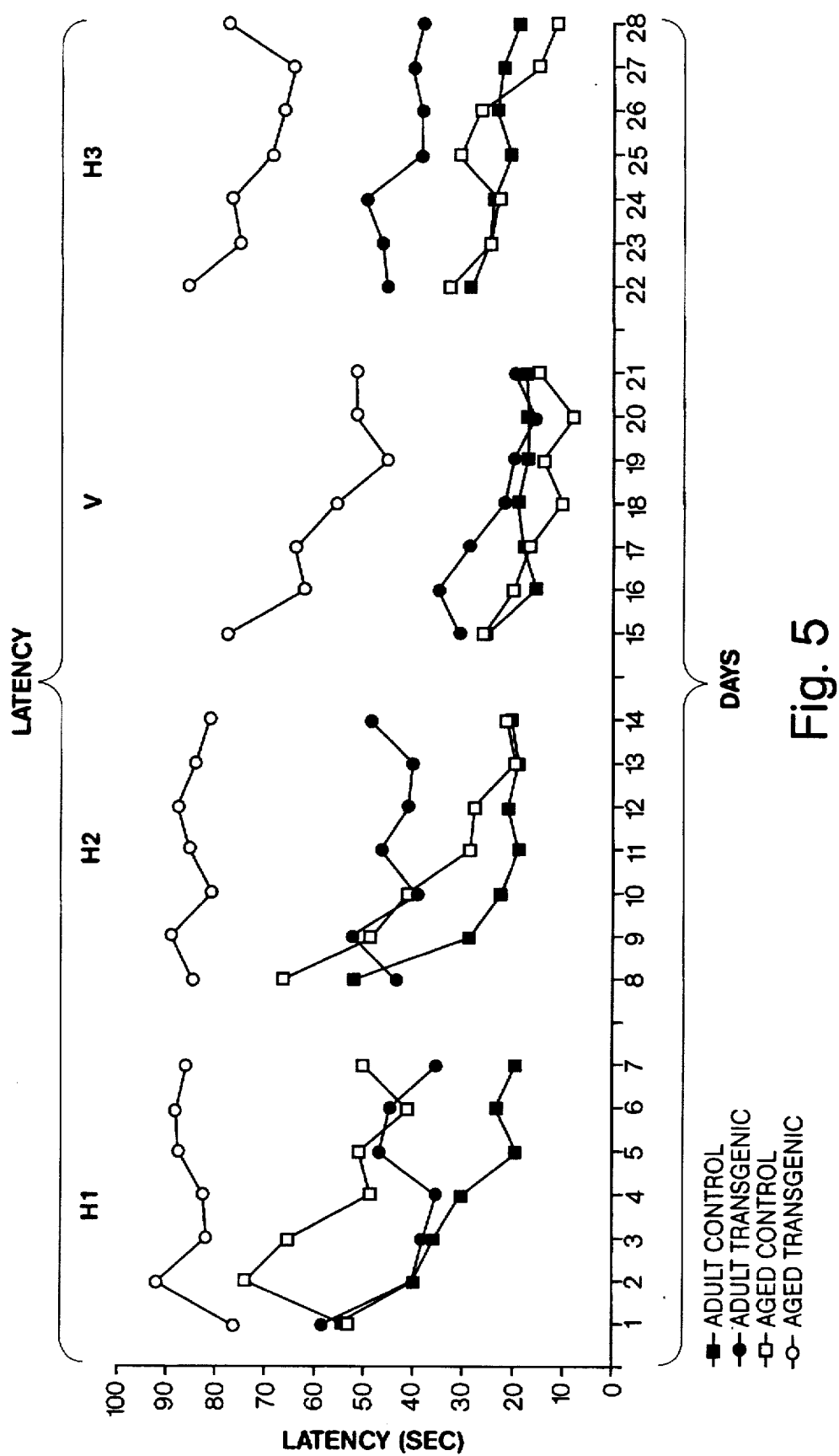
FIG. 5 is a graph summarizing the results of spatial memory tasks performed on adult and aged, control and transgenic animals. These results are expressed as latency of time to reach a platform (as described herein). As shown, transgenic animals exhibited significant spatial-impairment as compared to age-matched controls; in adult animals, however, cued task performance did not differ from that of controls, indicating that increased latency in the transgenic animals was due to impaired memory alone. In older animals, cued task deficits appeared to be more significant in transgenic animals than in controls.

To demonstrate that the expression of the NFL/C-100 APP construct was confined to the nervous system, RNA was isolated from various tissues and analyzed by Northern blotting. In the three preferred transgenic lines described above, C-100 APP messenger RNA (of about 1 kb) was detected in the cortex (C), cerebellum (Cb), and spinal cord (S), and was absent from liver (L), heart (H), kidney (K), lung (Lu), and adrenals (A) (FIG. 4). Each lane contained equivalent amounts of RNA as indicated by hybridization to a ribosomal RNA probe (18S) used as a control.

Figure 7A:
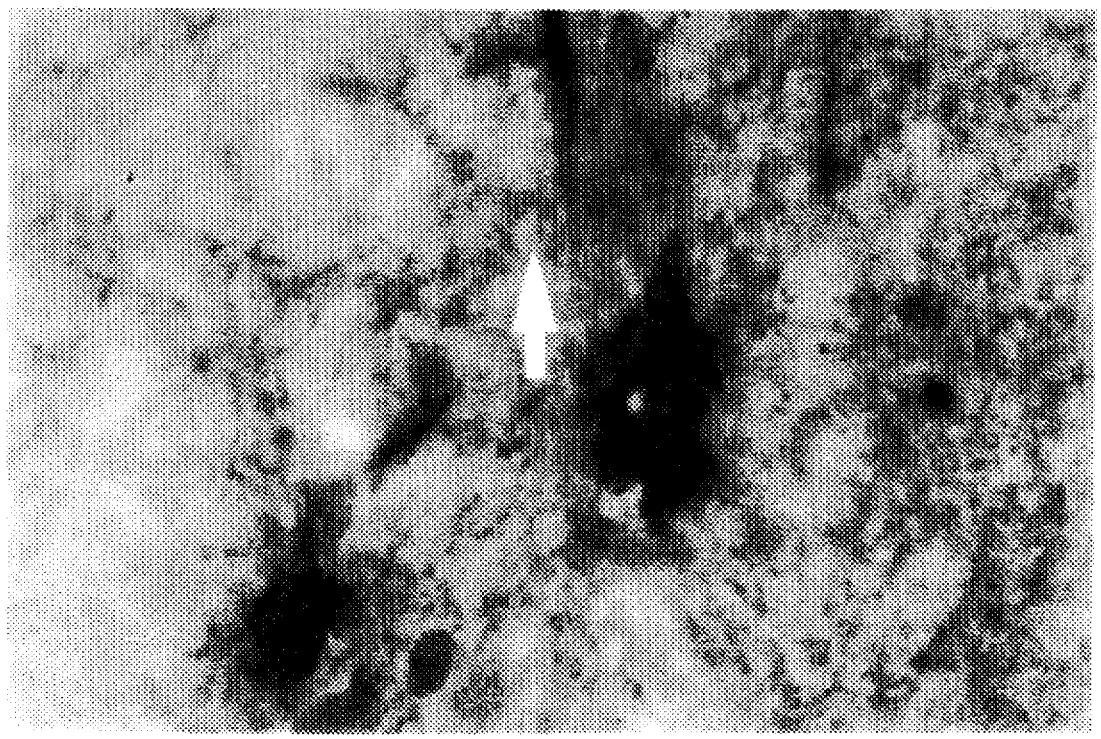
FIGS. 7A and 7B are a set of photomicrographs showing transgenic (FIG. 7A) and control (FIG. 7B) mouse brain sections processed for immunocytochemistry using an anti-amyloid antibody (R1282; available from Dr. Dennis Selkoe; Harvard Medical School). Eight month old transgenic animals exhibited increased numbers of beta-amyloid accumulations as compared to control animals. As shown, control animals also routinely exhibited moderate levels of staining with anti-amyloid antibody.
Figure 7B:
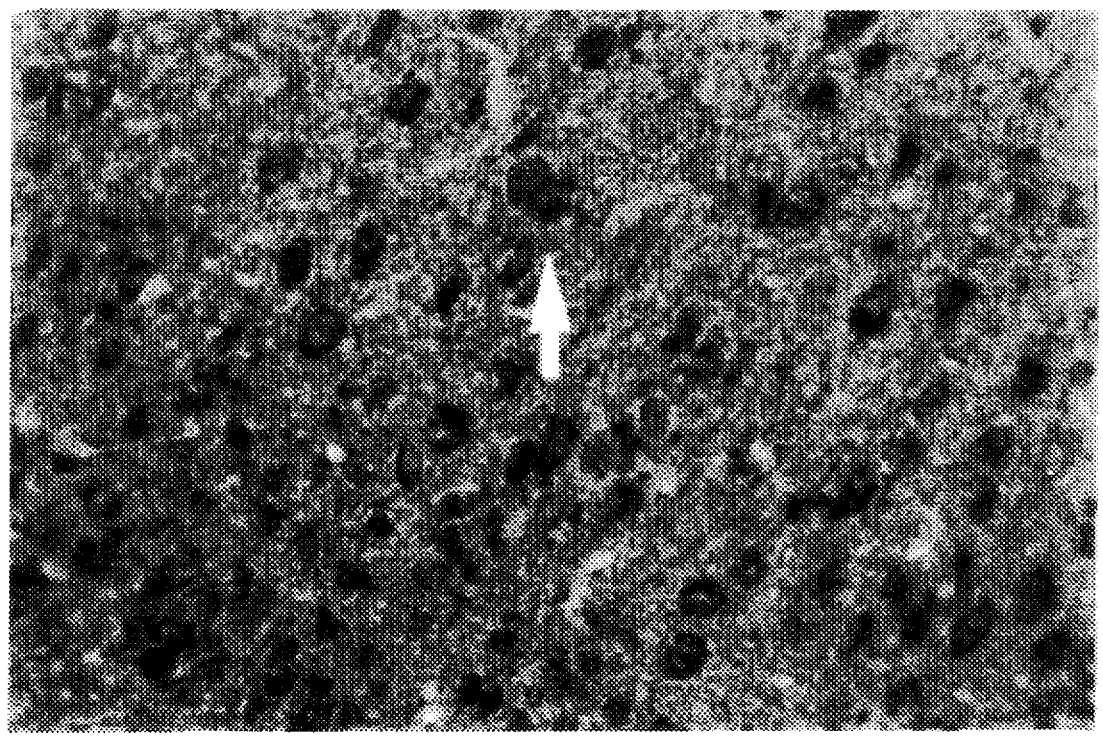

Detection of Increased Anti-Amyloid Protein Immunoreactivity in the Brains of C-100 APP Transgenic Mice To determine whether expression of the NFL/C-100 APP construct resulted in an increase in amyloid accumulation in the brain tissues of transgenic mice, immunocytochemistry was performed using antibodies specific for beta-amyloid protein. The transgenic mice described above were anesthetized by an intraperitoneal injection of chlorohydrate and then perfused through the heart with a 4% solution of buffered paraformaldehyde. The brain was removed and postfixed for 1 hour with 4% buffered paraformaldehyde, followed by an overnight incubation in a 20% solution of sucrose in buffered saline. The tissue was then preserved by freezing at −40° C. and stored at −70° C. Sections were cut on a cryostat at a thickness of 15 microns, placed on slides, and processed for immunohistochemistry using the Vectastain ABC kit for rabbit polyclonal antibodies (available from Dimension Laboratories, Mississauga, Ontario). The anti-amyloid antibody (R1282) was provided by Dr. Dennis Selkoe of Harvard Medical School. The results of these experiments indicated that areas of increased accumulation of beta-amyloid existed in the brains of transgenic mice when compared to equivalent controls. These experiments were carried out using 12 mice which were monitored at between 9 and 18 months of age (i.e., both adult and aged). As shown in FIGS. 7A and 7B, extracellular and intracellular immunoreactivity was observed in the cortex of transgenic animals (FIG. 7A), whereas solely intracellular staining was observed in the control animals (FIG. 7B) (as expected because the antibody also recognized the full-length precursor protein).

Increases in Reactive Astrocytes in the Brains of C-100 APP Transgenic Mice

Astrocytic reactions are often observed following various forms of brain injury (Eddleston and Mucke, Neuroscience 54:15–36, 1993). To assess whether the expression of the NFL/C-100 APP transgene resulted in pathological changes in brain tissue, immunocytochemical staining was carried out using an antibody directed against glial fibrillary acidic protein (GFAP), a marker of astrocytes. Well known features of Alzheimer's disease include regions of gliosis (i.e., reactive astrocytes identified by anti-GFAP immunoreactivity) surrounding deposits of amyloid in senile plaques, as well as overall increases in GFAP levels, as compared to normal brain tissue (Frederickson, Neurobiology of Aging 13:239–253, 1992).

Figure 8A:
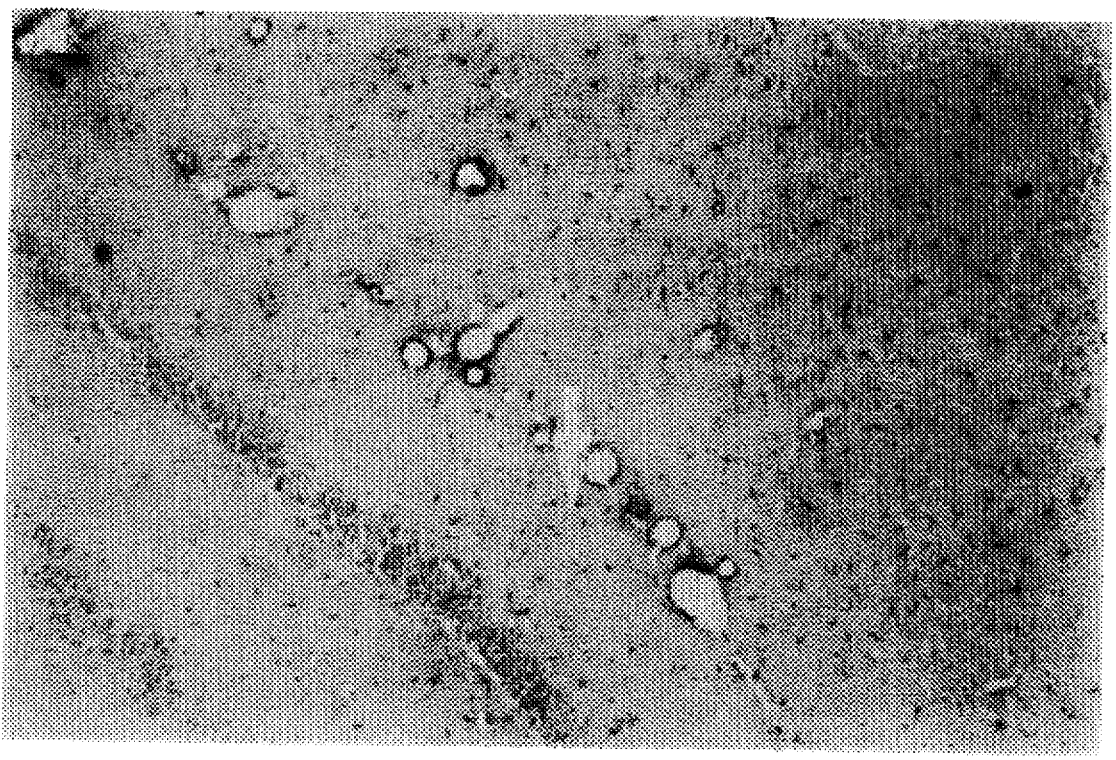
FIGS. 8A, 8B, 8C, and 8D are a set of photomicrographs showing control (FIGS. 8A and 8C) and transgenic (FIGS. 8B and 8D) mouse brain sections from the hippocampus/cortex processed for immunocytochemistry using anti-glial fibrillary acidic protein (GFAP) antibody (from Dako; Dimension Laboratories; Mississauga, Ontario). As shown, transgenic animals exhibited increases in both the size and reactivity of GFAP-positive astrocytes as compared to controls. This increased gliosis in transgenic animals was also observed at the higher magnifications shown in FIGS. 8C and 8D.
Figure 8B:
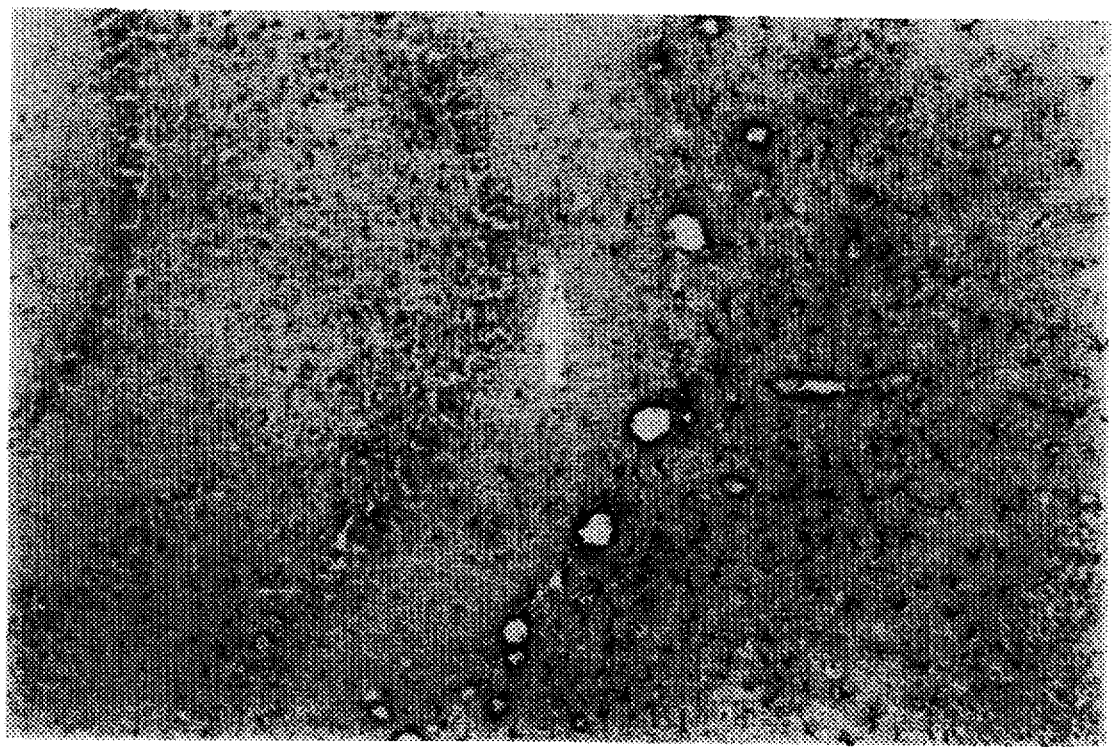
Figure 8C:
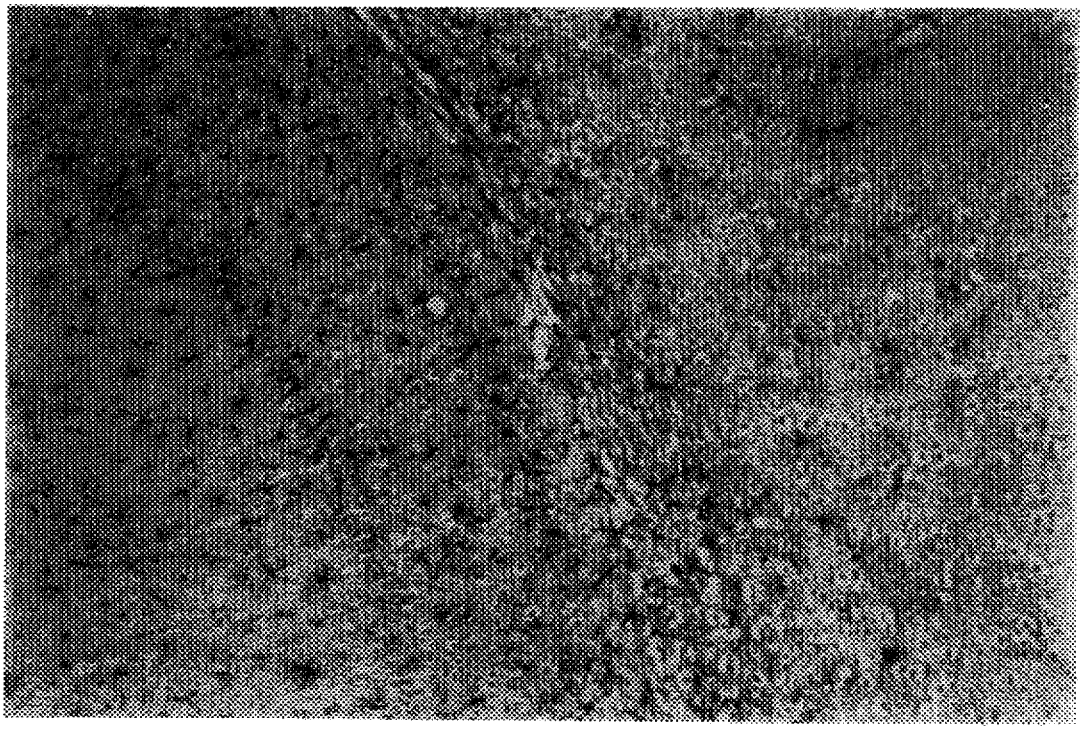
Figure 8D:
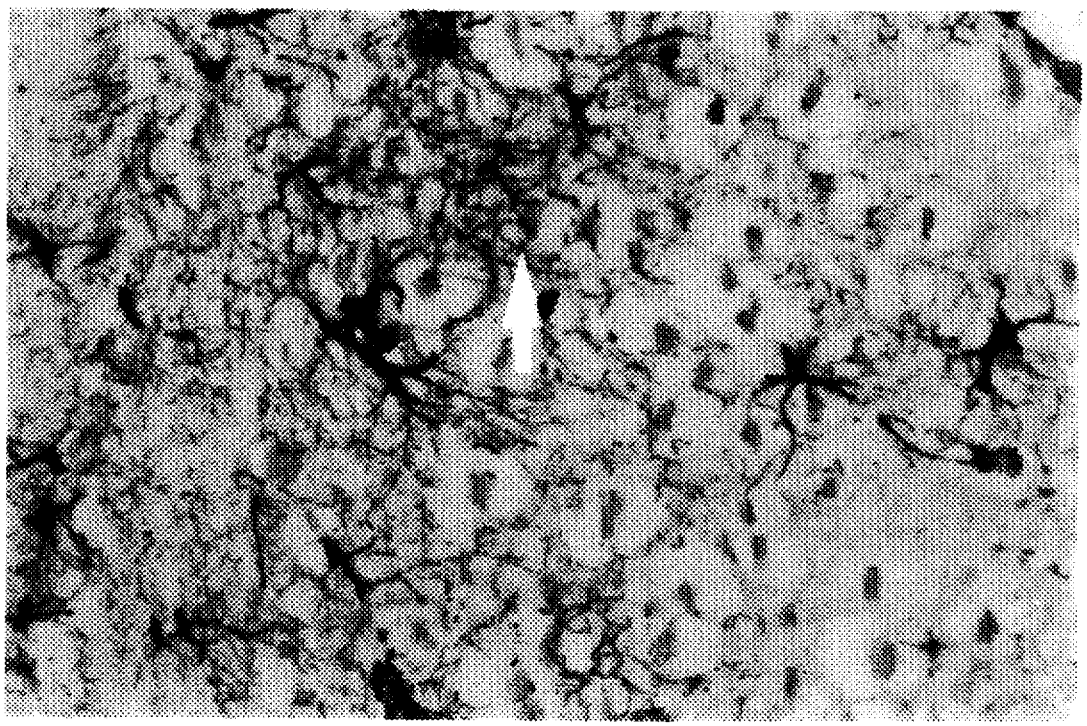

Briefly, these experiments were carried out using a GFAP-specific antibody obtained from Dako (Dimension Laboratories, Mississauga, Ontario) at a dilution of 1:10, 000. The immunohistochemistry was carried out according to the manufacturer's instructions, with signals detected using the horseradish peroxidase substrate, aminoethylcarbazol (Dimension Laboratories, Mississauga, Ontario), a material which produces a reddish insoluble product upon reaction. Sections were counterstained with hematoxylin (Fisher Scientific, Montreal, Quebec). In all comparison groups of different ages, the transgenic mice described above exhibited increased staining with anti-GFAP antibody, as compared to control mice. These experiments were carried out with transgenic and control animals, and tests were conducted at 4 months, 9 months, and 18 months of age. The data are shown in FIGS. 8A–8D. As indicated, transgenic animals (FIGS. 8A and 8C) exhibited increased GFAP-positive astrocytes when compared to control animals (FIGS. 8B and 8D).

Microglial Activation in the Brains of C-100 APP Transgenic Mice

Figure 9A:
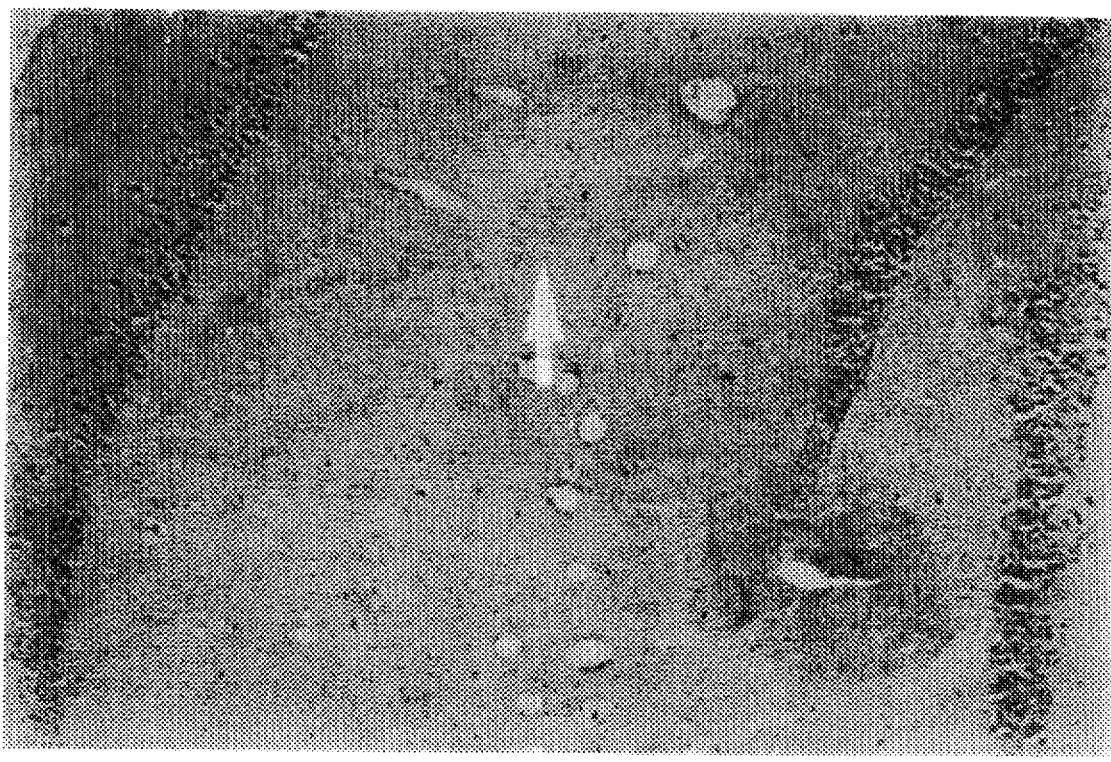
FIGS. 9A, 9B, 9C, and 9D are a set of photomicrographs showing control (FIGS. 9A and 9C) and transgenic (FIGS. 9B and 9D) mouse brain sections from the hippocampus processed for immunocytochemistry using an anti-Mac-1 antibody (prepared from the supernatant of the rat hybridoma M1/70.15.11.5.HL; ATCC). In groups of transgenic animals of differing ages, increased numbers of Mac-1 microglia were observed in comparison to control animals. An increase in Mac-1 microglia in transgenic animals was also observed at the higher magnifications shown in FIGS. 9C and 9D.
Figure 9B:
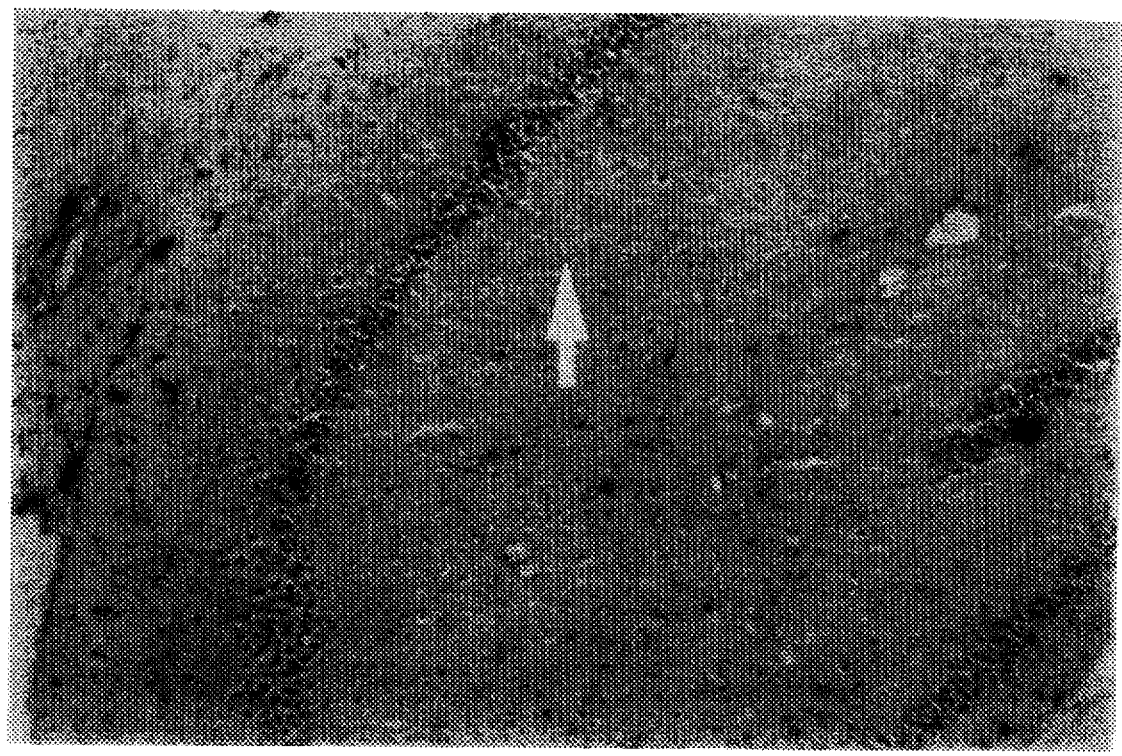
Figure 9C:
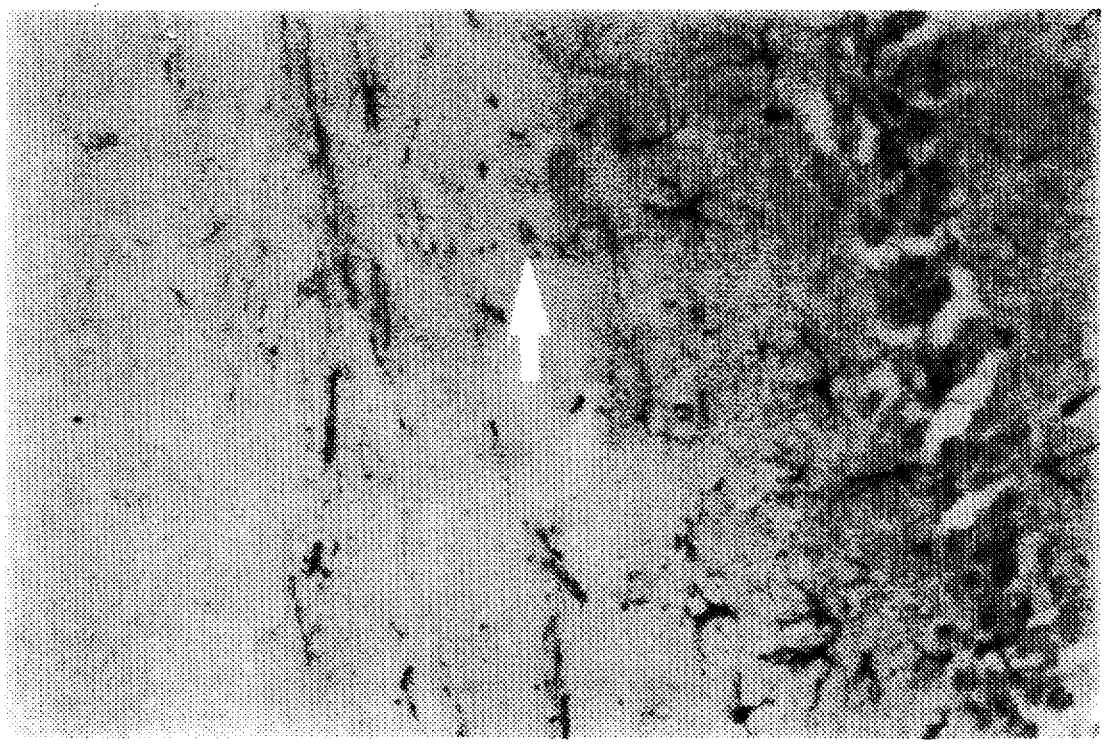
Figure 9D:
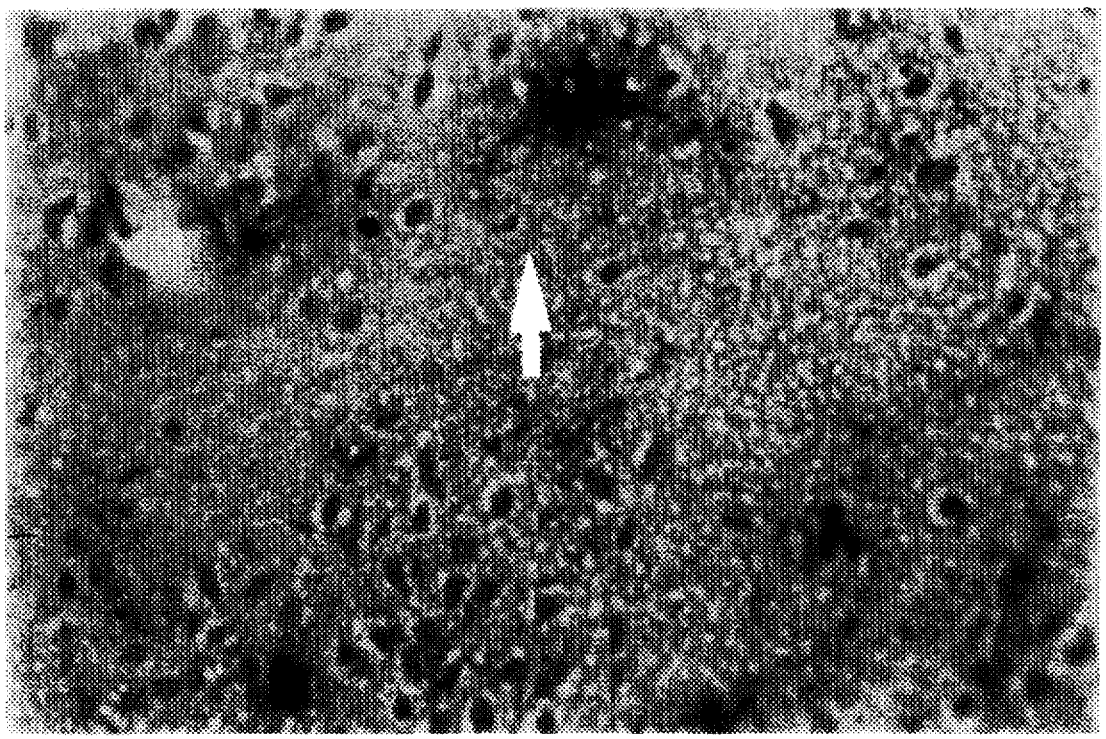

Microglial activation has been implicated in the pathology of Alzheimer's disease (Mrak et al., Human Pathology 26:816–823, 1995). Microglia (the macrophages which reside in brain) have been shown to become activated (i.e., capable of mediating an immune response) in the presence of amyloid protein. To determine whether microglia were present in the brains of the transgenic mice of the invention, cryostat sections were prepared from the brains of the transgenic and control mice and reacted with a macrophage-specific antibody, specifically, the anti-Mac-1 antibody (prepared from the supernatant of the rat hybridoma M1/70.15.11.5.HL; ATCC, Rockland, Md.). This antibody, which was used at a dilution of 1:9, reacts against the subunit antigen (complement receptor type 3) in mouse and man. A secondary anti-rat antibody conjugated to horseradish peroxidase (Dimension Laboratories, Mississauga, Ontario) was used to reveal specific staining. In all comparison groups of different ages (i.e., 4 months, 9 months, and 18 months), the transgenic mice possessed between a 30–50% increase in anti-Mac-1-positive microglia relative to control mice. These data are shown in FIGS. 9A–9D. As indicated, increased numbers of Mac-1 microglia were observed in transgenic animals (FIGS. 9B and 9D) in comparison to control animals (FIGS. 9A and 9C).

Figure 10:
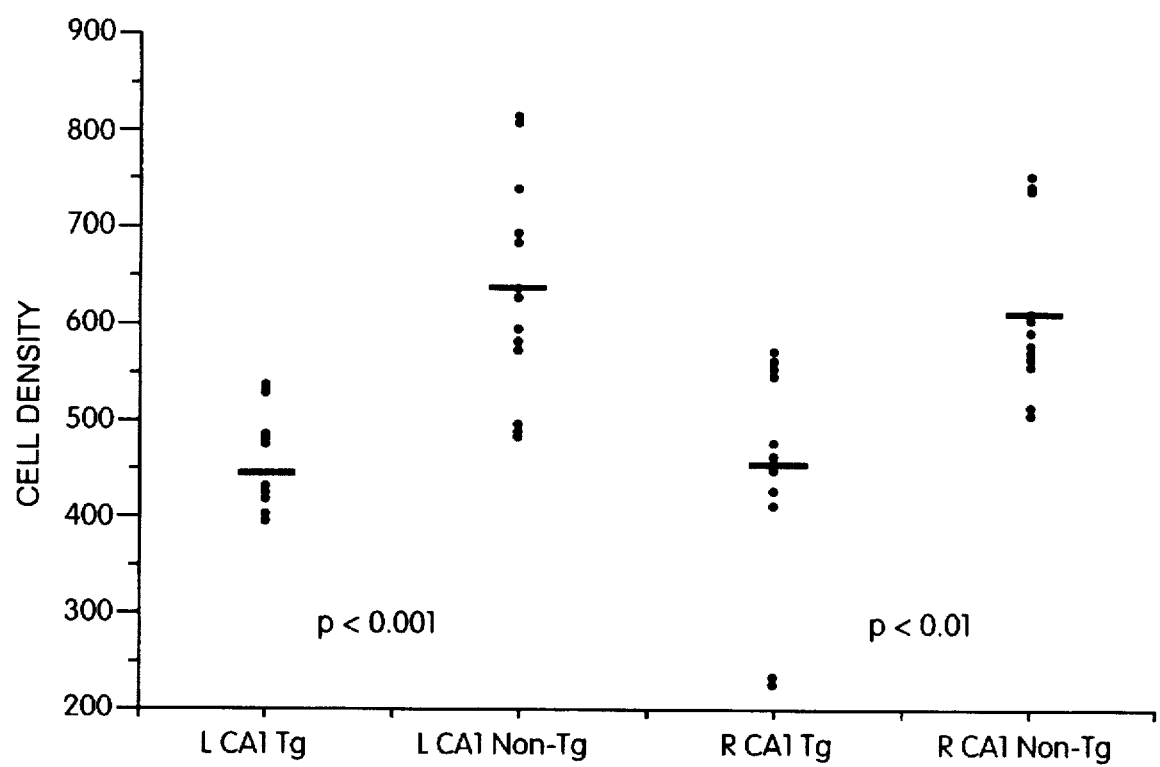
FIG. 10 is a graph summarizing data on hippocampal cell density in aged control ("Non-Tg") and transgenic ("Tg") mouse brain sections stained with cresyl. Neuron density in the CA1 region of the hippocampus of transgenic animals was found to be significantly lower than in control animals. "L" represents left and "R" represents right hippocampal formations.

Neuronal Cell Loss in the CA1 Region of the Hippocampus of C-100 APP Transgenic Mice Alzheimer's disease is characterized by the loss of neurons, particularly in the hippocampus and neocortex. To examine neuronal numbers in the transgenic animals described above, 15 micron cryostat sections from brains obtained from aged mice (18 months old) were stained with cresyl violet (Fisher Scientific, Montreal, Quebec) as a neuron detection agent. Numbers of neurons in the CA1 region of each half of the hippocampus were counted on 4 adjacent sections as described previously. The area of counted cells was then quantitated by image analysis (Meaney, Science 239:766–768, 1988), and the results expressed as cells per area. As shown in FIG. 10, the transgenic mice, on average, had 15% to 20% fewer neurons than the equivalent control mice. In these experiments, 10 transgenic and 11 control animals were studied.

Behavioral Characterization of C-100 APP Transgenic Mice

To assess the behavioral characteristics of transgenic mice expressing the C-100 APP fragment, a circular plastic tub, of 170 cm in diameter and 70 cm in height, was filled with water (at 20° C.) up to the 45 cm level, and used as a maze. The inside of the maze was lined with white colored plastic, and, for purposes of analysis, the maze was divided into four quadrants of equal sizes, denoted I, II, III, and IV (positioned in the same order as a Cartesian plane). For the testing phase, rectangular cues (22×28 cm) with differing geometric patterns were placed at 3 cm above the water level, at each of four locations between the quadrants. A square Plexiglas platform (22 cm on a side) was placed in the center of a quadrant, with the selection of the quadrant depending on the tasks required during each phase. During all phases, a mild powder was added to the water to make it opaque. A videocamera above the maze recorded the path swum by each mouse, and the path was stored by computer for further analysis. The lighting in the water maze was constant.

Before experimental testing began, a training phase was administered to the mice to assess whether the animals could swim and whether they could climb onto the platform. In this training phase, a plexiglas alley with one closed end was placed inside the water maze, with the platform located at the opposite, open end. Mice were placed into the water at the closed end of the alley and allowed to swim to the platform. The procedure was repeated eight consecutive times a day. No cues were present during this training. Testing began the day following a successful determination that all test animals could swim to and climb onto the platform eight consecutive times.

During the testing phase, each mouse was placed in the water facing the wall of the tank at one of the four starting points located in the center of each quadrant. Each mouse was allowed to swim for 120 seconds. If a mouse did not climb onto the platform by the end of this maximum period, it was placed onto the platform by hand. Each mouse was given a 30 second rest period before the next swim began, and each mouse was given eight swims a day. Starting point sequences were chosen pseudo-randomly such that each starting point was used twice, and all behavioral tests were carried out without knowledge as to group membership.

To assess the animal's behavioral characteristics, the following experimental design was utilized. Mice were tested for 28 days on two tasks: a hidden platform task which tested for spatial learning, and a visible platform task which assessed cued learning. The study was divided into four blocks of seven days each. The first task, escape to a hidden platform, spanned the first two blocks and the last block. The platform remained in the same location from day to day within a single block, but was located in different positions for each block of experiments. Visible platform testing was carried out in the third test block, during which time the platform was moved to a new location every day. During hidden platform testing, the platform was located 1 cm below the water's surface, in the middle of a quadrant. During visible platform testing, the platform was made visible to the mice by raising it 0.5 cm above the water's surface, by putting black tape around the platform's edge, and by adding a black cylinder (of 7 cm in diameter and 12 cm in height) to the platform's center.

Four measures were used to assess the performance of mice: (i) latency, or the time that the mouse spent in the water before finding the platform; (ii) the total distance swum by the mouse during a trial (i.e., "total distance"); (iii) the mean distance from the platform swum by the mouse (i.e., "mean distance"), calculated as the average of the distance of the animal from the center of the platform at every 200 msec interval; and (iv) the number of times that a mouse found the platform (i.e., "trials correct"). The daily individual averages across trials for all measures were calculated at the end of the last trial by computer analysis of stored data, and these averages were used in the final analysis.

The four measures selected for analysis reflected different aspects of performance.

"Latency" is a standard measure of learning in studies using a water maze paradigm, as well as in many behavioral tasks measuring performance of humans and other mammals.

The "total distance" measure is also useful for studying learning because it does not take speed into account, and it therefore discerns performance of mice mainly in terms of strategy. In one particular illustrative example, in a subset of animals that show identical latencies, a difference in performance may be observed by the length of the swim path; slower animals, for example, may follow a more accurate path to the platform, while faster swimming animals may reach the platform first but be less accurate in their search. A decreased swimming distance represents increased accuracy.

"Mean distance" is another measure which discerns differences in strategy abilities, specifically in relationship to an animals' proximity to the platform. For example, animals with the same latencies or total distances may present different search patterns; some may visit every point in the water maze indiscriminately, while others may swim closer to the platform yet be unable to locate it. This difference in pattern may indicate that some animals preserve certain learning abilities better than others.

Finally, the "trials correct" measure is an alternative test useful in instances of poor performance and where no discrimination among the above measures is evident. This test also provides information regarding intertrial differences that other measures do not indicate. By this test, even when performance of animals in an average of eight trials may be the same according to the first three measures, some animals in a group may reach the platform more often than others. For example, certain animals with a mean latency of about 100 seconds may infrequently locate the platform, while others with the same latency period locate the platform, albeit at the end of a trial. Similarly, although the mean and total distances swum by animals may be identical, some animals may find the platform while others do not.

In all behavioral experiments, data collected according to the above four measures were analyzed by a four-way determination of variance (ANOVA). The factors considered in the analysis were (i) group (transgenic or control), (ii) age (adult or aged), (iii) type of task ("task"; cued or visual learning), and (iv) day.

The results for all measures are shown in FIG. 6. As indicated, a significant effect was observed for the transgenic animals of the invention for each of the four factors in every behavioral measure tested. Aged mice were impaired relative to adult mice. Transgenic mice were impaired relative to control animals. All mice (transgenic and non-transgenic) performed better in cued task than in spatial task experiments; and performance of all mice improved within blocks of testing.

Other Embodiments

Transgenic animals of the invention include those which express an Alzheimer's-associated protein in the nervous system of the animal, thereby producing a model system for the study of Alzheimer's disease and the screening of useful therapeutics. Preferably, the expressed Alzheimer's-associated protein is an amyloid protein (for example, an amyloid precursor or an amyloid fragment, such as the C-100 fragment). Other proteins which may be expressed in these animals include, without limitation, all or a portion of the apolipoprotein E protein or the proteins of presenilin 1 (S182) or presenilin 2 (STM2).

In general, specific DNA sequences, which have been shown to be involved in Alzheimer's disease, such as that coding for the last 100 amino acids of the amyloid precursor protein (APP), that coding for the apolipoprotein E4 isotype, or others, may be obtained by isolation from genomic sources, by preparation of cDNAs from isolated mRNA templates, by direct chemical synthesis, or by some combination of these techniques. Once obtained, the Alzheimer's-associated gene may be specifically inserted within the first exon position (for example, as described herein) of the human neurofilament gene using the techniques described herein as a means to generate adult transgenic animals with progressive and specific spatial impairments concomitant with neuropathological features of Alzheimer's disease. As described herein, the sequence generally will possess its own termination codon; in addition or alternatively, a polyadenylation site may be added following the coding sequence. The use of the NFL construct and method described herein provides for central nervous system-specific expression of the transgene in the adult animal and generation of transgenic animals with behavioral and neuropathological phenotype resembling Alzheimer's disease.

What is claimed is:

1. A transgenic mouse whose genome comprises a nucleic acid sequence encoding the C-terminal 100 amino acids of the human β-amyloid precursor protein (C-100 APP) inserted into exon I of the neurofilament gene such that all or part of exon I has been deleted and whose genome expresses said nucleic acid sequence under the control of the neurofilament L-gene regulatory region, and wherein expression of the nucleic acid sequence results in said mouse exhibiting an increased amyloid accumulation and at least one phenotype from the group consisting of an increase in reactive astrocytes, an increased microglial activation, a decreased number of neurons and spatial memory impairment.

2. The transgenic mouse of claim 1, said expression of said C-100 APP-encoding nucleic acid sequence being limited to all or a part of said mouse's nervous system.

3. The transgenic mouse of claim 1, said mouse exhibiting an increase in amyloid accumulation in the central nervous system.

4. The transgenic mouse of claim 3, said mouse exhibiting an increase in amyloid accumulation in the brain.

5. The transgenic mouse of claim 1, said mouse exhibiting spatial memory impairment.

6. The transgenic mouse of claim 1, said mouse exhibiting no substantial motor defects.

7. The transgenic mouse of claim 5, said spatial memory impairment progressively worsening with the age of said mouse.

8. The transgenic mouse of claim 5, said mouse exhibiting no substantial anxiety.

9. The transgenic mouse of claim 1, said mouse exhibiting an increase in reactive astrocytes in the brain.

10. The transgenic mouse of claim 1, said mouse exhibiting an increase in microglial activation.

11. The transgenic mouse of claim 1, said mouse exhibiting a decreased number of neurons.

12. The transgenic mouse of claim 11, said mouse exhibiting at least a 15% decrease in neurons in the hippocampus.

13. The transgenic mouse of claim 5, said mouse being capable of transferring said spatial memory impairment trait to its offspring in a Mendelian fashion.

14. A method of producing a transgenic mouse that exhibits a spatial memory impairment, said method comprising (a) introducing into a fertilized oocyte of said mouse a nucleic acid sequence encoding the C-terminal 100 amino acids of the human C-100 APP inserted into exon I of the neurofilament gene such that all or part of exon I has been deleted and said nucleic acid sequence is expressed under the control of the neurofilament L-gene regulatory region;

(b) transplanting said fertilized oocyte into a pseudopregnant mouse;

(c) allowing said fertilized oocyte to develop to term;

(d) identifying at least one offspring containing said nucleic acid sequence encoding human C-100 APP, and wherein said offspring exhibit a spatial memory impairment.

15. A transgene comprising a nucleic acid sequence encoding the C-terminal 100 amino acids of the human β-amyloid precursor protein (C-100 APP) inserted into exon I of the neurofilament gene such that all or part of exon I has been deleted and said nucleic acid sequence is under the control of the neurofilament L-gene regulatory region.

16. A method of testing a substance for efficacy in the treatment of Alzheimer's disease, said method comprising exposing a transgenic mouse of claim 1 to said substance and determining the extent of spatial memory impairment exhibited by said mouse following substance exposure, a decrease in said spatial memory impairment indicating a substance useful for the treatment of Alzheimer's disease.

* * * * *

UNITED STATES PATENT AND TRADEMARK OFFICE
CERTIFICATE OF CORRECTION

PATENT NO. 5,894,078
DATED      April 13, 1999
INVENTORS  Josehine Nalbantoglu, Jean-Pierre Julien, and Matthew Shapiro It is certified that error appears in the above-identified patent and that said Letters Patent is hereby corrected as shown below:

In col. 6, line 15, replace "MRNA" with --mRNA--.

In col. 6, line 18, replace "polya-extended RNA" with --polyA-extended RNA--.

In col. 6, line 22, replace "MRNA" with --mRNA--.

In col. 6, line 23, replace "MRNA" with --mRNA--.

In col. 6, line 34, replace "PNFL" with --pNFL--.

In col. 6, line 48, replace "MRNA" with --mRNA--.

In col. 6, line 53, replace " MRNA" with --mRNA--.

In col. 6, line 53, replace "P-amyloid-derived" with --β-amyloid-derived--.

In col. 8, line 5, replace "PSVL" with --pSVL--.

In col. 8, line 10, replace "CDNA" with --cDNA--.

In col. 8, line 39, replace "CDNA" with --cDNA--.

Signed and Sealed this

Fourteenth Day of December, 1999

Attest:

Q. TODD DICKINSON

Attesting Officer

Acting Commissioner of Patents and Trademarks